US012664313B2

(12) United States Patent
Fraser et al.

(10) Patent No.: US 12,664,313 B2
(45) Date of Patent: Jun. 23, 2026

(54) UTILITY PRESERVING ANONYMIZATION OF VISUAL CONTENT

(71) Applicant: INTERNATIONAL BUSINESS MACHINES CORPORATION, Armonk, NY (US)

(72) Inventors: Kieran Fraser, Dublin (IE); Liubov Nedoshivina, Dublin (IE); Anisa Halimi, Dublin (IE); Stefano Braghin, Dublin (IE)

(73) Assignee: International Business Machines Corporation, Armonk, NY (US)

( * ) Notice: Subject to any disclaimer, the term of this patent is extended or adjusted under 35 U.S.C. 154(b) by 221 days.

(21) Appl. No.: 18/524,419

(22) Filed: Nov. 30, 2023

(65) Prior Publication Data

US 2025/0181770 A1     Jun. 5, 2025

(51) Int. Cl.
*G06F 21/62* (2013.01)
*G16H 40/67* (2018.01)

(52) U.S. Cl.
CPC ......... *G06F 21/6263* (2013.01); *G16H 40/67* (2018.01)

(58) Field of Classification Search
None
See application file for complete search history.

(56) References Cited

U.S. PATENT DOCUMENTS

| | | | |
|---|---|---|---|
| 8,463,006 B2 | 6/2013 | Prokoski | |
| 10,535,120 B2 | 1/2020 | Edwards | |
| 10,803,347 B2 | 10/2020 | Salavon | |
| 11,520,923 B2 | 12/2022 | Sohn | |
| 2013/0060579 A1* | 3/2013 | Yu | H04L 63/08 705/3 |
| 2019/0279765 A1* | 9/2019 | Giataganas | G16H 10/60 |
| 2020/0312457 A1 | 10/2020 | Kasthurirathne | |
| 2023/0137378 A1 | 5/2023 | Laterza | |
| 2023/0186098 A1 | 6/2023 | Chang | |

(Continued)

FOREIGN PATENT DOCUMENTS

| | | |
|---|---|---|
| CN | 112836653 A | 5/2021 |
| JP | 2006320488 A | 10/2011 |

OTHER PUBLICATIONS

Alslman, et al., "Hybrid Encryption Scheme for Medical Imaging Using AutoEncoder and Advanced Encryption Standard", MDPI, Electronics 2022, 11, 3967, Published Nov. 30, 2022, 15 pgs.

(Continued)

*Primary Examiner* — Jeffrey R Swearingen
(74) *Attorney, Agent, or Firm* — Elliot J. Shine

(57) ABSTRACT

A method, computer system, and a computer program product for visual content privatization is provided. The present invention may include receiving visual content associated with a subject. The present invention may include altering the visual content using at least one or more image perturbations or one or more adversarial patches in response to a practitioner requesting an external consultation from a third party. The present invention may include presenting an altered visual content to the practitioner within a user interface. The present invention may include transmitting the altered visual content to the third party following an approval by the practitioner.

19 Claims, 3 Drawing Sheets

(56)          References Cited

U.S. PATENT DOCUMENTS

| | | | |
|---|---|---|---|
| 2024/0394408 A1* | 11/2024 | Schmidtlein | ........... G16H 30/20 |
| 2025/0239366 A1* | 7/2025 | Ayodhimani | .......... G16H 50/20 |

OTHER PUBLICATIONS

Antonatos, et al., "PRIMA: An End-to-End Framework for Privacy at Scale", ResearchGate, Apr. 2018, 13 pgs.

Brown, et al., "Adversarial Patch", arXiv:1712.09665v2 [cs.CV], May 17, 2018, 6 pgs.

Bruna, et al., "Modified MRI Anonymization (De-Facing) for Improved MEG Coregistration", MDPI, Bioengineering 2022, 9, 591, Published Oct. 21, 2022, 15 pgs.

Carlini, et al., "Towards Evaluating the Robustness of Neural Networks", 2017 IEEE Symposium on Security and Privacy, IEEE Computer Society, 2017, pp. 39-57.

Chatterjee, et al., "Classification of Brain Tumours in MR Images Using Deep Spatiospatial Models", arXiv:2105.14071v2 [eess.IV], Jan. 14, 2022, 13 pgs.

Chen, et al., "HopSkipJumpAttack: A Query-Efficient Decision-Based Attack", arXiv:1904.02144v5 [cs.LG], Apr. 28, 2020, 18 pgs.

De Sitter, et al., "Facing Privacy in Neuroimaging: Removing Facial Features Degrades Performance of Image Analysis Methods", Springer, European Radiology (2020) 30:1062-1074, 13 pgs.

DLIB, "High Quality Face Recognition with Deep Metric Learning", DLIB C++ Library, Feb. 12, 2017, 40 pgs.

DLIB, "Major Features", DLIB C++ Library, [accessed Sep. 6, 2023], 4 pgs., Retrieved from the Internet: <http://dlib.net/>.

Ghiasi, et al., "Breaking Certified Defenses: Semantic Adversarial Examples with Spoofed Robustness Certificates", arXiv:2003.08937v1 [cs.LG], Mar. 19, 2020, 16 pgs.

Goodfellow, et al., "Explaining and Harnessing Adversarial Examples", arXiv:1412.6572v3 [stat.ML], Mar. 20, 2015, pp. 1-11.

He, et al., "Deep Residual Learning for Image Recognition", arXiv:1512.03385v1 [cs.CV], Dec. 10, 2015, pp. 1-12.

Jeong, et al., "De-Identification of Facial Features in Magnetic Resonance Images: Software Development Using Deep Learning Technology", J Med Internet Res Dec. 2020; 22(12):e27739, Published online Dec. 10, 2020, 16 pages.

Jeong, et al., "De-Identification of Facial Features in Magnetic Resonance Images: Software Development Using Deep Learning Technology", Journal of Medical Internet Research 2020;22(12):e22739, 8 pgs.

Knoche, et al., "Octuplet Loss: Make Face Recognition Robust to Image Resolution", arXiv:2207.06726v2 [cs.CV], Mar. 21, 2023, 14 pgs.

Lee, et al., "On Physical Adversarial Patches for Object Detection", ICML 2019 Workshop on Security and Privacy of Machine Learning, arXiv:1906.11897v1 [cs.CV], Jun. 20, 2019, 5 pgs.

Letournel, et al., "Face De-Identification With Expressions Preservation", 2015 IEEE Internationl Conference on Image Processing (ICIP), Quebec City, Canada, 2015, pp. 4366-4370, 6 pgs.

Liu, et al., "Deep Face-Swap Model Combining Attention Mechanism and CycleGAN", Journal of Physics: Conference Series, 2278 (2022) 012037, 10 pgs.

Madry, et al., "Towards Deep Learning Models Resistant to Adversarial Attacks", arXiv:1706.06083v4 [stat.ML] Sep. 4, 2019, 28 pgs.

Oh, et al., "Adversarial Image Perturbation for Privacy Protection A Game Theory Perspective", 2017 IEEE International Conference on Computer Vision, pp. 1491-1500.

Parks, et al., "Automated Facial Recognition of Computed Tomography-Derived Facial Images: Patient Privacy Implications", Springer, J DIgit Imaging (2017) 30:204-214, 11 pgs.

Popescu, et al., "Obfuscation Algorithm for Privacy-Preserving Deep Learning-Based Medical Image Analysis", MDPI, Applied Sciences 2022, 12, 3997, Published Apr. 14, 2022, 26 pgs.

Rakpurkar, et al., "CheXNet: Radiologist-Level Pneumonia Detection on Chest X-Rays with Deep Learning", arXiv:1711.05225v3 [cs.CV], Dec. 25, 2017, 7 pgs.

Ryu, et al., "Adversarial Attacks by Attaching Noise Markers on the Face Against Deep Face Recognition", Elsevier, Journal of Information Security and Applications 60 (2021) 102874, May 21, 2021, 11 pgs.

Schwarz, et al., "Face Recognition from Research Brain PET: An Unexpected PET Problem", Elsevier, NeuroImage 258 (2022) 119357, Jun. 3, 2022, 11 pgs.

Terhorst, et al., "QMagFace: Simple and Accurate Quality-Aware Face Recognition", arXiv:2111.13475v3 [cs.CV], Mar. 23, 2022, 16 pgs.

Ter-Sarkisov, "Detection and Segmentation of Lesion Areas in Chest CT Scans for the Prediction of COVID-19", Computer Society, ASCEE, Science in Information Technology Letters, vol. 1., No. 2, Nov. 2020, pp. 92-99.

Tesseract OCR, "Various Documents Related to Tesseract OCR", Tesseract OCR, [accessed Sep. 5, 2023], 5 pgs., Retrieved from the Internet: <https://tesseract-ocr.github.io/docs/>.

Torfi, "Privacy-Preserving Synthetic Medical Data Generation with Deep Learning", Doctor of Philosophy Dissertation, Virginia Polytechnic Institute and State University, Aug. 10, 2020, 115 pgs.

Xiao, et al., "Improving Transferability of Adversarial Patches on Face Recognition with Generative Models", 2021 IEEE/CVF Conference on Computer Vision and Pattern Recognition (CVPR), 10 pages.

Xue, et al., "Face Image De-Identification by Feature Space Adversarial Perturbation", Wiley, Concurrency Computat Pract Exper. 2023;35:e7554, 13 pgs.

Yang, et al., "A Digital Mask to Safeguard Patient Privacy", Nature Medicine, vol. 28, Sep. 2022, 1883-1892, 22 pgs.

Zhong, et al., "Face Transformer for Recognition", arXiv:2103.14803v2 [cs.CV], Apr. 13, 2021, 5 pgs.

Zhu, et al., "Human Recognition Using Face in Computed Tomography", arXiv:2005.14238v1 [cs.CV], May 28, 2020, 11 pgs.

\* cited by examiner

100

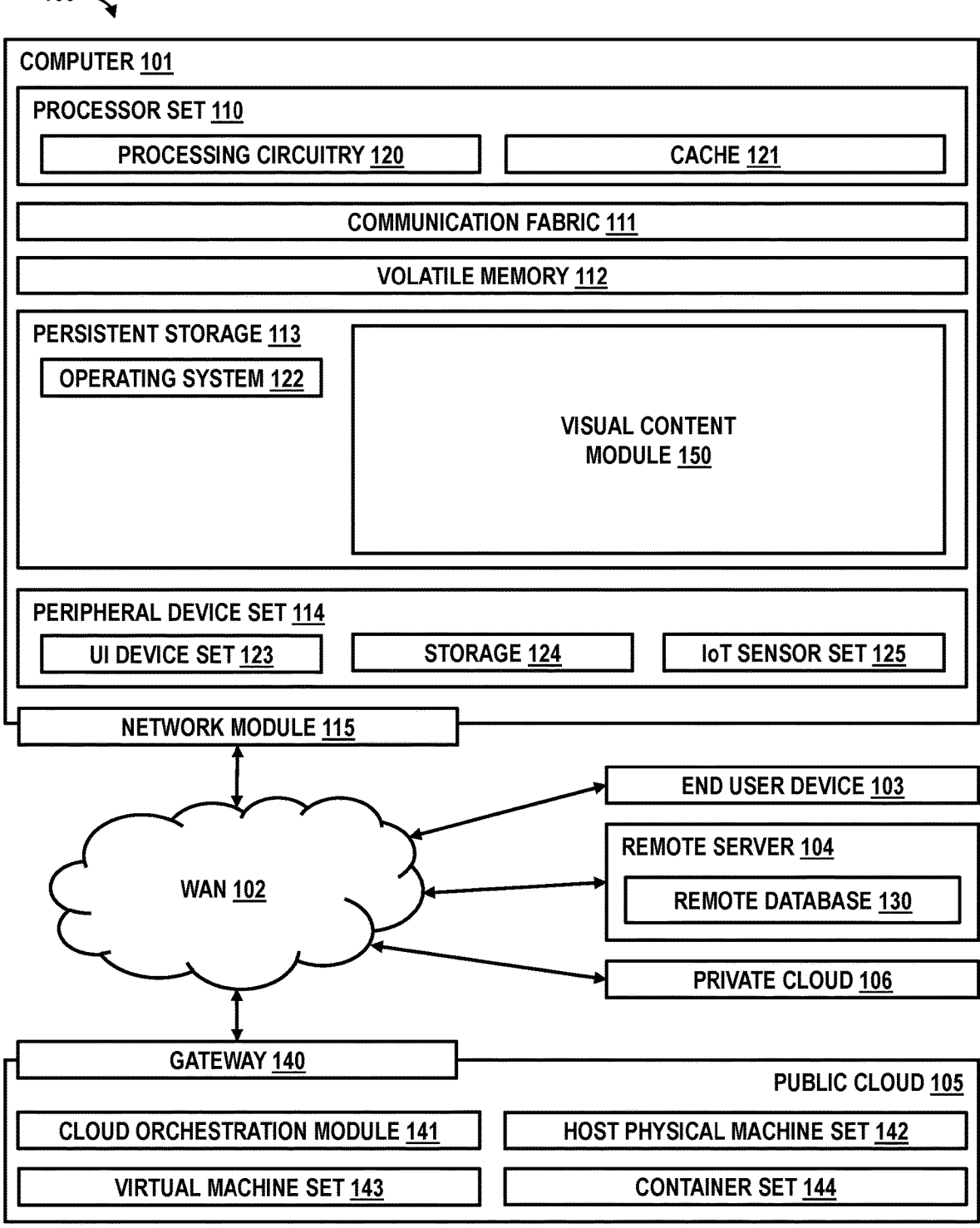

COMPUTER 101

PROCESSOR SET 110

PROCESSING CIRCUITRY 120                CACHE 121

COMMUNICATION FABRIC 111

VOLATILE MEMORY 112

PERSISTENT STORAGE 113

OPERATING SYSTEM 122

VISUAL CONTENT
MODULE 150

PERIPHERAL DEVICE SET 114

UI DEVICE SET 123        STORAGE 124        IoT SENSOR SET 125

NETWORK MODULE 115

WAN 102

END USER DEVICE 103

REMOTE SERVER 104

REMOTE DATABASE 130

PRIVATE CLOUD 106

GATEWAY 140

PUBLIC CLOUD 105

CLOUD ORCHESTRATION MODULE 141        HOST PHYSICAL MACHINE SET 142

VIRTUAL MACHINE SET 143        CONTAINER SET 144

START

RECEIVE VISUAL CONTENT ASSOCIATED WITH A SUBJECT 202

ALTER THE VISUAL CONTENT ASSOCIATED WITH THE SUBJECT 204

PRESENT THE ALTERED VISUAL CONTENT TO A PRACTITIONER 206

TRANSMIT THE ALTERED VISUAL CONTENT TO A THIRD PARTY 208

UTILITY PRESERVING ANONYMIZATION OF VISUAL CONTENT

BACKGROUND

The present invention relates generally to the field of computing, and more particularly to visual content privatization.

As digital doctors and remote consultations become more widely adopted due to technology advances, there has accordingly been an increased need for sharing visual content of a subject, such as, but not limited to, medical images associated with a patient. However, within the healthcare domain medical practitioners may find it difficult to share visual content associated with patients due to risks that a patient may be re-identified using features present in the visual content, amongst other privacy constraints.

Accordingly, a method for anonymizing visual content such that the re-identification of a subject is reduced while simultaneously maintaining the utility of the visual content is required for parties to safely share visual content while maintaining privacy constraints.

SUMMARY

Embodiments of the present invention disclose a method, computer system, and a computer program product for visual content privatization. The present invention may include receiving visual content associated with a subject. The present invention may include altering the visual content using at least one or more image perturbations or one or more adversarial patches in response to a practitioner requesting an external consultation from a third party. The present invention may include presenting an altered visual content to the practitioner within a user interface. The present invention may include transmitting the altered visual content to the third party following an approval by the practitioner.

In another embodiment, the method may include displaying one or more prompts to the practitioner in the user interface, wherein the one or more prompts are designed to gather information about a downstream task.

In a further embodiment, the method may include presenting analytics associated with the altered visual content and one or more additional recommendations, wherein the analytics and the one or more additional recommendations are generated using one or more machine learning models; and retraining the one or more machine learning models based on the one or more additional recommendations implemented and not implemented by the practitioner.

In addition to a method, additional embodiments are directed to a computer system and a computer program product for altering visual content associated with a subject using at least perturbations, adversarial patches, and/or other noise applied by one or more machine learning models trained to maximize utility for a downstream task while reducing a re-identification risk of the visual content with respect to the subject.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE SEVERAL VIEWS OF THE DRAWINGS

These and other objects, features and advantages of the present invention will become apparent from the following detailed description of illustrative embodiments thereof, which is to be read in connection with the accompanying drawings. The various features of the drawings are not to scale as the illustrations are for clarity in facilitating one skilled in the art in understanding the invention in conjunction with the detailed description. In the drawings:

FIG. 1 depicts a block diagram of an exemplary computing environment according to at least one embodiment;

DETAILED DESCRIPTION

Figure 2:
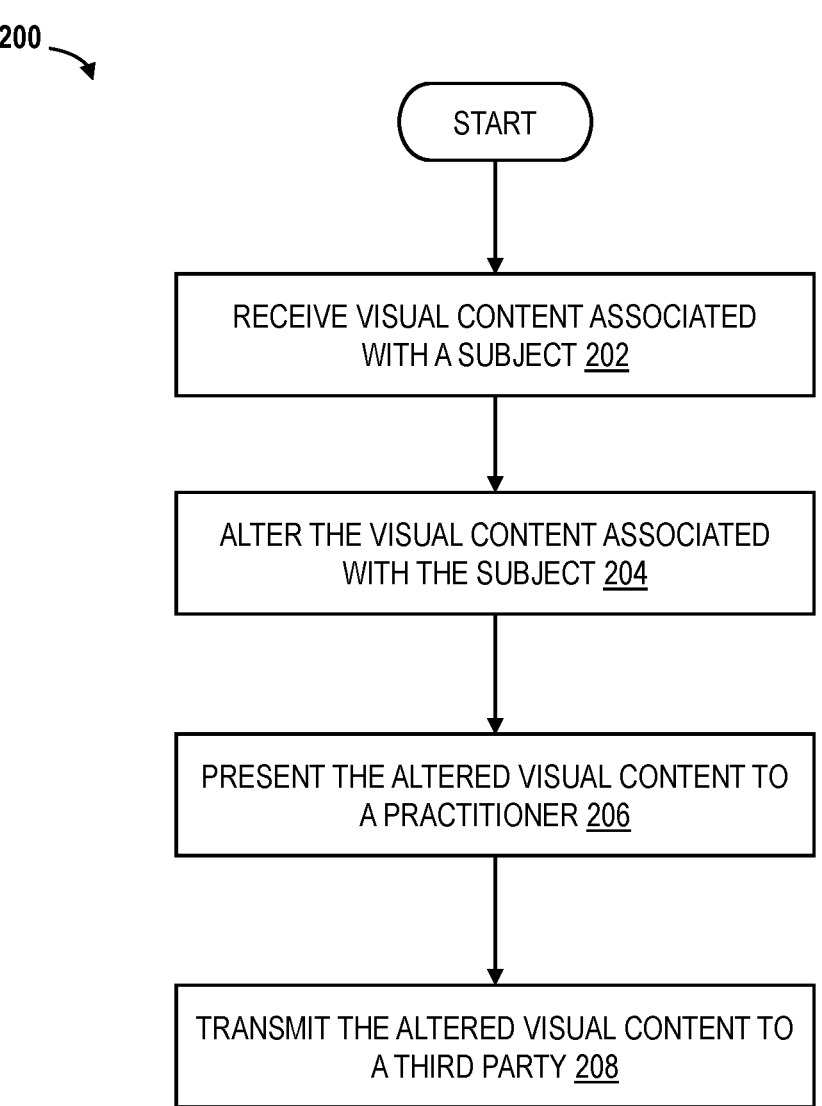
FIG. 2 is an operational flowchart illustrating a process for visual content privatization according to at least one embodiment.

The following described exemplary embodiments provide a system, method and program product for visual content privatization. As such, the present embodiment has the capacity to improve the technical field of visual content privatization by altering visual content associated with a subject using at least perturbations, adversarial patches, and/or other noise applied by one or more machine learning models trained to maximize utility for a downstream task while reducing a re-identification risk of the visual content with respect to the subject. More specifically, the present invention may include receiving visual content associated with a subject. The present invention may include altering the visual content in response to a practitioner requesting an external consultation from a third party. The present invention may include presenting an altered visual content to the practitioner within a user interface. The present invention may include transmitting the altered visual content to the third party following an approval by the practitioner.

As described previously, as digital doctors and remote consultations become more widely adopted due to technology advances, there has accordingly been an increased need for sharing visual content of a subject, such as, but not limited to, medical images associated with a patient. However, within the healthcare domain medical practitioners may find it difficult to share visual content associated with patients due to risks that a patient may be re-identified using features present in the visual content, amongst other privacy constraints.

Accordingly, a method for anonymizing visual content such that the re-identification of a subject is reduced while simultaneously maintaining the utility of the visual content is required for parties to safely share visual content while maintaining privacy constraints.

Therefore, it may be advantageous to, among other things, receive visual content associated with a subject, alter the visual content in response to a practitioner requesting an external consultation from a third party, present an altered visual content to the practitioner within a user interface, and transmit the altered visual content to the third party following an approval by the practitioner.

According to at least one embodiment, the present invention may improve the manner by which perturbations, adversarial patches, and/or other noise are added to the visual content for specific downstream tasks and/or specific practitioners.

According to at least one embodiment, the present invention may improve recommended edits displayed to a practitioner within the user interface and learn edits likely to be accepted by particular practitioners and/or for particular tasks such that the visual content module 150 may reduce the number of versions of the altered visual content presented to the user within the user interface and reduce the number of iterations visual content requires within the privacy-utility system.

According to at least one embodiment, the present invention may improve protecting of subject anonymity through the addition of adversarial patches, perturbations, and/or other noise to visual content associated with the subject while preserving utility associated with a downstream task.

According to at least one embodiment, the present invention may improve the altering of visual content, specifically medical images, by identifying regions of interest and/or regions of importance within the visual content such that the alterations maximize the trade-off between privacy and usefulness.

According to at least one embodiment, the present invention may improve the altering of visual content associated with subjects by leveraging adversarial algorithms and utility metrics as feedback such that an optimal type of noise suited for an identified or selected downstream task minimizes the disruption to areas of interest whilst maximizing interference with reidentification.

According to at least one embodiment, the present invention may improve the balance between privacy and downstream utility for visual content by providing quantifiable metrics which describe the current risk of reidentification for a particular image or video with respect to current state-of-the-art methods, the level of mitigation an identified optimal defense would provide, and a level of utility at differing rates of privacy.

According to at least one embodiment, the present invention may improve visual content altering by utilizing a threshold component which decides whether the visual content meets a minimum level of privacy with respect to balancing utility for downstream tasks. If the threshold is not met, the feature recognizers and visual content are passed to the visual content altering component of the privacy-utility system which adds or removes noise to the visual content as directed by the evaluation component. Noise that is added may be task dependent, including adversarial patches, masking, watermarking, or deepfake.

Referring to FIG. 1, Computing environment 100 contains an example of an environment for the execution of at least some of the computer code involved in performing the inventive methods, such as altering visual content associated with a subject using at least perturbations, adversarial patches, and/or other noise applied by one or more machine learning models trained to maximize utility for a downstream task while reducing a re-identification risk of the visual content with respect to the subject using the visual content module 150. In addition to module 150, computing environment 100 includes, for example, computer 101, wide area network (WAN) 102, end user device (EUD) 103, remote server 104, public cloud 105, and private cloud 106. In this embodiment, computer 101 includes processor set 110 (including processing circuitry 120 and cache 121), communication fabric 111, volatile memory 112, persistent storage 113 (including operating system 122 and module 150, as identified above), peripheral device set 114 (including user interface (UI) device set 123, storage 124, and Internet of Things (IoT) sensor set 125), and network module 115. Remote server 104 includes remote database 130. Public cloud 105 includes gateway 140, cloud orchestration module 141, host physical machine set 142, virtual machine set 143, and container set 144.

Computer 101 may take the form of a desktop computer, laptop computer, tablet computer, smart phone, smart watch or other wearable computer, mainframe computer, quantum computer or any other form of computer or mobile device now known or to be developed in the future that is capable of running a program, accessing a network or querying a database, such as remote database 130. As is well understood in the art of computer technology, and depending upon the technology, performance of a computer-implemented method may be distributed among multiple computers and/or between multiple locations. On the other hand, in this presentation of computing environment 100, detailed discussion is focused on a single computer, specifically computer 101, to keep the presentation as simple as possible. Computer 101 may be located in a cloud, even though it is not shown in a cloud in FIG. 1. On the other hand, computer 101 is not required to be in a cloud except to any extent as may be affirmatively indicated.

Processor Set 110 includes one, or more, computer processors of any type now known or to be developed in the future. Processing circuitry 120 may be distributed over multiple packages, for example, multiple, coordinated integrated circuit chips. Processing circuitry 120 may implement multiple processor threads and/or multiple processor cores. Cache 121 is memory that is located in the processor chip package(s) and is typically used for data or code that should be available for rapid access by the threads or cores running on processor set 110. Cache memories are typically organized into multiple levels depending upon relative proximity to the processing circuitry. Alternatively, some, or all, of the cache for the processor set may be located "off chip." In some computing environments, processor set 110 may be designed for working with qubits and performing quantum computing.

Computer readable program instructions are typically loaded onto computer 101 to cause a series of operational steps to be performed by processor set 110 of computer 101 and thereby effect a computer-implemented method, such that the instructions thus executed will instantiate the methods specified in flowcharts and/or narrative descriptions of computer-implemented methods included in this document (collectively referred to as "the inventive methods"). These computer readable program instructions are stored in various types of computer readable storage media, such as cache 121 and the other storage media discussed below. The program instructions, and associated data, are accessed by processor set 110 to control and direct performance of the inventive methods. In computing environment 100, at least some of the instructions for performing the inventive methods may be stored in module 150 in persistent storage 113.

Communication fabric 111 is the signal conduction path that allows the various components of computer 101 to communicate with each other. Typically, this fabric is made of switches and electrically conductive paths, such as the switches and electrically conductive paths that make up busses, bridges, physical input/output ports and the like. Other types of signal communication paths may be used, such as fiber optic communication paths and/or wireless communication paths.

Volatile memory 112 is any type of volatile memory now known or to be developed in the future. Examples include dynamic type random access memory (RAM) or static type RAM. Typically, volatile memory 112 is characterized by random access, but this is not required unless affirmatively indicated. In computer 101, the volatile memory 112 is located in a single package and is internal to computer 101, but, alternatively or additionally, the volatile memory may be distributed over multiple packages and/or located externally with respect to computer 101.

Persistent Storage 113 is any form of non-volatile storage for computers that is now known or to be developed in the future. The non-volatility of this storage means that the stored data is maintained regardless of whether power is being supplied to computer 101 and/or directly to persistent storage 113. Persistent storage 113 may be a read only memory (ROM), but typically at least a portion of the persistent storage allows writing of data, deletion of data and re-writing of data. Some familiar forms of persistent storage include magnetic disks and solid state storage devices. Operating system 122 may take several forms, such as various known proprietary operating systems or open source Portable Operating System Interface-type operating systems that employ a kernel. The code included in module 150 typically includes at least some of the computer code involved in performing the inventive methods.

Peripheral device set 114 includes the set of peripheral devices of computer 101. Data communication connections between the peripheral devices and the other components of computer 101 may be implemented in various ways, such as Bluetooth connections, Near-Field Communication (NFC) connections, connections made by cables (such as universal serial bus (USB) type cables), insertion-type connections (for example, secure digital (SD) card), connections made through local area communication networks and even connections made through wide area networks such as the internet. In various embodiments, UI device set 123 may include components such as a display screen, speaker, microphone, wearable devices (such as goggles and smart watches), keyboard, mouse, printer, touchpad, game controllers, and haptic devices. Storage 124 is external storage, such as an external hard drive, or insertable storage, such as an SD card. Storage 124 may be persistent and/or volatile. In some embodiments, storage 124 may take the form of a quantum computing storage device for storing data in the form of qubits. In embodiments where computer 101 is required to have a large amount of storage (for example, where computer 101 locally stores and manages a large database) then this storage may be provided by peripheral storage devices designed for storing very large amounts of data, such as a storage area network (SAN) that is shared by multiple, geographically distributed computers. IoT sensor set 125 is made up of sensors that can be used in Internet of Things applications. For example, one sensor may be a thermometer and another sensor may be a motion detector.

Network module 115 is the collection of computer software, hardware, and firmware that allows computer 101 to communicate with other computers through WAN 102. Network module 115 may include hardware, such as modems or Wi-Fi signal transceivers, software for packetizing and/or de-packetizing data for communication network transmission, and/or web browser software for communicating data over the internet. In some embodiments, network control functions and network forwarding functions of network module 115 are performed on the same physical hardware device. In other embodiments (for example, embodiments that utilize software-defined networking (SDN)), the control functions and the forwarding functions of network module 115 are performed on physically separate devices, such that the control functions manage several different network hardware devices. Computer readable program instructions for performing the inventive methods can typically be downloaded to computer 101 from an external computer or external storage device through a network adapter card or network interface included in network module 115.

WAN 102 is any wide area network (for example, the internet) capable of communicating computer data over non-local distances by any technology for communicating computer data, now known or to be developed in the future. In some embodiments, the WAN 102 may be replaced and/or supplemented by local area networks (LANs) designed to communicate data between devices located in a local area, such as a Wi-Fi network. The WAN and/or LANs typically include computer hardware such as copper transmission cables, optical transmission fibers, wireless transmission, routers, firewalls, switches, gateway computers and edge servers.

End User Device (EUD) 103 is any computer system that is used and controlled by an end user (for example, a customer of an enterprise that operates computer 101), and may take any of the forms discussed above in connection with computer 101. EUD 103 typically receives helpful and useful data from the operations of computer 101. For example, in a hypothetical case where computer 101 is designed to provide a recommendation to an end user, this recommendation would typically be communicated from network module 115 of computer 101 through WAN 102 to EUD 103. In this way, EUD 103 can display, or otherwise present, the recommendation to an end user. In some embodiments, EUD 103 may be a client device, such as thin client, heavy client, mainframe computer, desktop computer and so on.

Remote server 104 is any computer system that serves at least some data and/or functionality to computer 101. Remote server 104 may be controlled and used by the same entity that operates computer 101. Remote server 104 represents the machine(s) that collect and store helpful and useful data for use by other computers, such as computer 101. For example, in a hypothetical case where computer 101 is designed and programmed to provide a recommendation based on historical data, then this historical data may be provided to computer 101 from remote database 130 of remote server 104.

Public cloud 105 is any computer system available for use by multiple entities that provides on-demand availability of computer system resources and/or other computer capabilities, especially data storage (cloud storage) and computing power, without direct active management by the user. Cloud computing typically leverages sharing of resources to achieve coherence and economies of scale. The direct and active management of the computing resources of public cloud 105 is performed by the computer hardware and/or software of cloud orchestration module 141. The computing resources provided by public cloud 105 are typically implemented by virtual computing environments that run on various computers making up the computers of host physical machine set 142, which is the universe of physical computers in and/or available to public cloud 105. The virtual computing environments (VCEs) typically take the form of virtual machines from virtual machine set 143 and/or containers from container set 144. It is understood that these VCEs may be stored as images and may be transferred among and between the various physical machine hosts, either as images or after instantiation of the VCE. Cloud orchestration module 141 manages the transfer and storage of images, deploys new instantiations of VCEs and manages active instantiations of VCE deployments. Gateway 140 is the collection of computer software, hardware, and firmware that allows public cloud 105 to communicate through WAN 102.

Some further explanation of virtualized computing environments (VCEs) will now be provided. VCEs can be stored as "images." A new active instance of the VCE can be instantiated from the image. Two familiar types of VCEs are virtual machines and containers. A container is a VCE that uses operating-system-level virtualization. This refers to an operating system feature in which the kernel allows the existence of multiple isolated user-space instances, called containers. These isolated user-space instances typically behave as real computers from the point of view of programs running in them. A computer program running on an ordinary operating system can utilize all resources of that computer, such as connected devices, files and folders, network shares, CPU power, and quantifiable hardware capabilities. However, programs running inside a container can only use the contents of the container and devices assigned to the container, a feature which is known as containerization.

Private cloud 106 is similar to public cloud 105, except that the computing resources are only available for use by a single enterprise. While private cloud 106 is depicted as being in communication with WAN 102, in other embodiments a private cloud may be disconnected from the internet entirely and only accessible through a local/private network. A hybrid cloud is a composition of multiple clouds of different types (for example, private, community or public cloud types), often respectively implemented by different vendors. Each of the multiple clouds remains a separate and discrete entity, but the larger hybrid cloud architecture is bound together by standardized or proprietary technology that enables orchestration, management, and/or data/application portability between the multiple constituent clouds. In this embodiment, public cloud 105 and private cloud 106 are both part of a larger hybrid cloud.

According to the present embodiment, the computer environment 100 may use the visual content module 150 to altering visual content associated with a subject using at least perturbations, adversarial patches, and/or other noise applied by one or more machine learning models trained to maximize utility for a downstream task while reducing a re-identification risk of the visual content with respect to the subject. The visual content method is explained in more detail below with respect to FIG. 2.

Referring now to FIG. 2, an operational flowchart illustrating the exemplary visual content privatization process 200 used by the visual content module 150 according to at least one embodiment is depicted.

At 202, the visual content module 150 receives visual content associated with a subject. The visual content received by the visual content module 150 may include medical images, medical videos, amongst other visual content, which may include, but is not limited to including Magnetic Resonance Imaging (MRI) scans, Computed Tomography (CT) scans, X-ray images, ultrasounds, Positron Emission Tomography (PET) scans, Arthrograms, Myelograms, amongst other medical visual content. The visual content module 150 may utilize the one or more different scans described above in generating one or more medical images. As will be explained in more detail below, while the invention description may refer to medical images and/or medical videos the invention may apply more broadly to other visual content for which the anonymity of the subject may be desired while preserving the utility of the visual content, geographical images and/or maps, product images, proprietary images, images within internal documentation, images received as part of an identification verification process, amongst other visual content in which preserving anonymity may be desired. All of the visual content and/or other content associated with the subject received by the visual content module 150 shall not be construed as to violate or encourage the violation of any local, state, federal, or international law with respect to privacy protection. The visual content module 150 may receive consent from the subject and/or a practitioner within the user interface prior to receive any visual content.

The visual content received by the visual content module 150 may be stored in a database 130 which may utilize a private cloud and/or a protected local database of a medical institution in preserving the privacy of the visual content. A practitioner may access the visual content received through a user interface from one or more authorized devices. All of the visual content received may be secured and/or maintained by a cloud based service, such as, but not limited to, IBM Cloud® (IBM Cloud® and all IBM-based trademarks are trademarks or registered trademarks of International Business Machines Corporation in the United States, and/or other countries), amongst other cloud based services. The cloud based service may utilize, public cloud, private cloud, and/or hybrid cloud in securing at least the visual content, the user interface, and/or the one or more tools which may be utilized by the practitioner, such as a Digital Imaging and Communications in Medicine ("DICOM") and Picture Archiving and Communication System ("PACS"). DICOM may be a standard format that enables medical professionals to view, store, and share medical images irrespective of their geographic location or the devices they use, as long as those devices support the DICOM format. The images, along with the corresponding patient data, may be stored in a large database called a PACS. A physician using a DICOM viewer may have the ability to use many tools in order to examine an image, including, but not limited to, zooming, cropping, brightening, contrasting, calculating area measurements, and performing image enhancement.

At 204, the visual content module 150 alters the visual content associated with the subject. The visual content module 150 may alter the visual content associated with the subject received at step 202 in response to the practitioner requesting an external consultation and/or third-party opinion on the visual content and/or transmit the visual content associated with the subject from the database 130. The practitioner may indicate the desire to request the external consultation and/or third-party opinion with respect to the visual content in the user interface. In response to receiving the request from the practitioner the visual content module 150 may request additional details with respect to information which the practitioner aims to receive from the external consultation and/or third-party opinion. The visual content module may request the additional details from the practitioner within the user interface utilizing one or more prompts and/or visual displays. The prompts and/or visual displays may require a series of button clicks, swipes, input responses, and/or interactions with the visual content associated with the subject by the practitioner within the user interface. The one or more prompts presented within the user interface by the visual content module 150 may be designed to gather additional information with respect to a downstream task, which will be described in greater detail below. For example, the practitioner may utilize the visual display to identify portions of the images for which the practitioner desires the external consultation and/or third party opinion. As will be explained in more detail below, the visual content module 150 may alter the visual content associated with the subject utilizing a privacy-utility system designed to maximize utility while preserving privacy. Utility, in the context of the healthcare domain, may represent the ability of practitioners to successfully continue their diagnosis using the visual content associated with the subject. Privacy, in the context of the healthcare domain, may refer to the risk of being able to re-identify a subject using features present in medical images and/or medical videos, amongst other visual content. These privacy concerns may be even more prevalent in the digital age due to the abilities of Artificial Intelligence (AI) models trained on such images and/or videos and their abilities to re-identify.

In response to the request received from the practitioner in the user interface, the visual content module 150 may retrieve the visual content associated with the subject from the database 130. The visual content module 150 may alter the visual content associated with the subject utilizing a privacy-utility system introduced above. As will be explained in more detail below, the visual content module 150 may utilize image perturbations and/or adversarial patches amongst other methods in altering the visual content associated with the subject. Image perturbations may involve small changes and/or modifications to visual content, such as, but not limited to, altering color, brightness, adding noise, and/or applying filters, amongst other modifications. The degree of alterations, locations, and pervasiveness may be throttled depending on the use case and/or the responses to the prompt responses received from the practitioner. Adversarial patches may involve a small carefully designed image patch that may be added to the visual content for the purpose of causing an image classifier to misclassify the image to which it has been appended. Adversarial patches may typically be designed to be visually inconspicuous and may be placed in various positions within the visual content to be effective. The privacy-utility system may leverage adversarial algorithms and/or utility metrics as feedback to identify the optimal type of altering modifications suited for a selected downstream task that may minimize the disruption to areas of interest while maximizing interference for reidentification attempts, wherein the selected downstream task may be identified by the practitioner within the user interface and/or in response to the prompts presented to the practitioner by the visual content module 150. The one or more adversarial algorithms utilized by the visual content module 150, which may be described in more detail below, may utilize different types of evasion attacks (e.g., adversarial examples) which may attempt to identify an optimal amount of noise to add to the visual content module such that a trained classification model made misclassify the visual content. Evasion attacks (e.g., adversarial examples) may consist of carefully perturbing input samples such that at test time the input samples may be misclassified by a trained classification model, which may be evaluated in a plurality of scenarios by the visual content module 150, such as, but not limited to, not under attack and/or under attack. Each of the adversarial algorithms described below may identify an optimal amount of noise using different methods and/or facilitate a different representation of the noise added to the visual content.

The one or more adversarial machine learning algorithms which may be utilized by the visual content module 150 may include, but are not limited to including, a Fast Gradient Method and/or Fast Gradient Sign Method (FGSM), Adversarial Patch attacks, and/or Shadow attacks, amongst other adversarial attacks algorithms which may be utilized in making changes to input data, such as the visual content described at 202 and/or sample visual content utilized by the visual content module 150 in order to deceive a machine learning model, and/or train the classification model. For example, in the case of FGSM, during the attack the gradients of a loss function with respect to the input visual content are computed and may be utilized to create new visual content which may maximize the loss for the classification model. The FGSM model may be utilized by the visual content module 150 for training the against attacks which may be imperceptible to humans. Continuing with the above example, the visual content module 150 may utilize the adversarial patch attacks in further improving upon the FGSM attacks by enabling a patch of noise to be created which may work across multiple forms of visual content, such as, but not limited to, multiple images. This may be achieved by optimizing the noise across multiple images and/or transformations, which may again maximize the loss for the classification model. The adversarial patch attacks, unlike the FGSM method, may be perceivable to humans, however, the patches may be of different size and shape and may be inconspicuously added, either digitally or in the real world, such as by a practitioner utilizing the one image analysis tools described in greater detail above at step 202. In a final example, the visual content module 150 may also leverage shadow attacks, these attacks may apply larger perturbations that place images and/or other forms of visual content far from a class boundary whilst maintaining the imperceptibility of added perturbations. The visual content module 150 may utilize the shadow attack for its added benefit of fooling classification models which may be certified against some adversarial attacks (e.g., evasion attacks).

The privacy-utility system utilized by the visual content module 150 may be comprised of several components, including, but not limited to, a feature recognition component, an evaluation component, a threshold component, and/or a visual content altering component. Some of these components will be explained in greater detail below with respect to at least step 206 as well as FIG. 3. The feature recognition component may receive as input the visual content associated with the subject and/or altered visual content associated as well as ground truth data associated with the subject. The privacy-utility system may run one or more iterations of the cycle through the privacy-utility system until either a threshold may be exceeded and/or a maximum number of iterations may be met. The ground truth data associated with the subject may include known data and/or characteristics associated with the subject and/or other visual content associated with the subject stored in the database 130 and/or provided by the practitioner. The ground truth data associated with the subject may not be utilized by the visual content model without first receiving consent from the subject. The feature recognition component may utilize one or more feature recognition algorithms and/or one or more feature re-identification algorithms in accessing an initial privacy risk associated with the visual content associated with the subject. The one or more feature recognition algorithms which may be utilized by the visual content module within the feature recognition component may include, but are not limited to including, Python® face recognition, Python® deepface, FaceTransformer, QMagFace, amongst other Convolutional Neural Networks (CNNs) and/or Computer-Vision based feature recognition algorithms which may be implemented using Python® (Python® and all Python®-based trademarks are trademarks or registered trademarks of The Python Software Foundation (PSF) in the United States, and/or other countries). Python® face recognition-Residual Network (ResNet) may be a standard CNN architecture that may be enriched with skip connections to reuse activations of previous layers, which may allow an increase in the number of layers (i.e., the depth of the network) and improve the network's performance, for example, in feature recognition. For example, when applied to visual content the algorithm may initialize a detection stage in which a region of interest (ROI) is extracted. It may then utilize the extracted content in predicting a label for the extracted ROI. The model may utilize a plurality of visual content as input for which the labels are known, such as visual content associated with a plurality of subjects stored in database 130. The label of the unseen image and/or visual content may be predicted by comparing the new image and/or visual content to the existing images and/or visual content maintained within database 130. Python® deepface is a library which may be utilized by the visual content module, the library may include a set of state of the art feature recognition and feature attribute analysis methos. Python® deepface may also be comprised of various CNN architectures which may be utilized in training the one or more machine learning models utilized by the visual content module 150 as part of the privacy-utility system in a supervised manner such that they may predict the identity of the subject associated with the visual content and/or other attributes of the subject associated with the visual content such that the visual content module 150 may narrowly and specifically apply the perturbations, alterations, and/or other noise within the visual content altering component of the privacy-utility system. While feature recognition models may typically represent images as multi-dimensional vectors, Python® deepface may contain a function which takes as input an image and/or other visual content and a CNN model name and return embeddings of the image and/or other visual content. By computing the distance between the embeddings of the images and/or other visual content using similarity metrics, such as, but not limited to, cosine similarity, Euclidean distance, amongst other similarity metrics the visual content module 150 may leverage Python® deepface in feature verification and/or feature recognition. Python® deepface may also be comprised of an attributes analysis module which includes various features that may be present within the subjects for which the visual content is received at step 202. This attributes analysis module may be utilized to predict the features of the subject associated with the visual content by querying a corresponding CNN model, wherein the corresponding CNN model may be trained based on a labeled attributes dataset stored within the database 130. The visual content module 150 may further leverage FaceTransformer and QMagFace. FaceTransformer may be a method which uses the transformer architecture for the attribute recognition task. An input image and/or visual content may be split into a set of overlapping patches. The set of patches may then be encoded to an image and/or other visual content embedding and concatenated with the position embeddings as well as a learnable embedding such as a class token (e.g., label from a set of classes, identification of a full name in the set). The obtained embeddings may then be passed to an attention mechanism and then to a Multi-Layer Perceptron, and trained in a supervised manner to solve a classification task, such as, predict an identity class of the subject associated with the visual content. The attention layer of the trained model may reveal the relevant attribute areas. QMagFace (e.g., Quality-aware face recognition) approach may utilize facial recognition models such as, but not limited to, ResNet, and may improve their performance especially in cross-age and/or cross-pose cases via proposed quality-aware comparison function (e.g., MagFace loss), which may reflect an identity similarity. The proposed loss function may be adjusted to a face recognition and/or other attribute recognition model's specificity in certain cases (e.g., variations in performance for different subject features) to calculate a similarity score between a pair of images and/or other forms of visual content, the image embeddings may be derived from the face recognition and/or other attribute recognition model (i.e., the last layer of the ResNet model). The one or more feature recognition algorithms described above may be utilized alone and/or in combination by the visual content module within the feature recognition component of privacy-utility system. The visual content module 150 may also leverage additional feature recognition algorithms beyond the ones described above depending on the visual content associated with the subject received at step 202.

The one or more feature re-identification algorithms may consist of a class of neural networks such as a Siamese Neural Network (SNN) which contains two or more identical sub-networks, such that the sub-networks may have the same configuration with the same parameters and/or weights wherein the feature vector in the SNN is created using a CNN which is learned with a labeled dataset. The feature re-identification algorithms utilizes an image embedding process such that vectors assigned to an image may have close embedding vectors with similar images according to a defined distance, the defined distance may be defined according to a Euclidean distance, cosine similarity, amongst other visual content distance metrics. The feature recognition component of the privacy-utility system may also extract any metadata associated with the visual content, such as, but not limited to, medical notes, and use one or more privacy tools in protecting any sensitive information and/or personal identifiable information within the metadata from the visual content. The one or more privacy tools may include, but are not limited to including, type identification, masking providers, privacy risk assessments, and/or anonymization providers, amongst other privacy tools which may be implemented using, for example, the IBM® Data-Privacy Toolkit (IBM® and all IBM®-based trademarks are trademarks or registered trademarks of International Business Machines Corporation in the United States, and/or other countries). The goal of the one or more feature recognition algorithms which may be utilized by the visual content module 150 may include determining whether the identity of the subject associated with the visual content may be identified or not. While the terms re-identification algorithms and feature recognition algorithms may be referenced separately above, the terms may refer to similar algorithms and/or methods utilized by the visual content module 150 within the privacy-utility system. Although one may apply any of the feature recognition methods described previously and verify that the subject may not be identified. Both the re-identification algorithms and feature recognition algorithms may utilize similar tooling, i.e., the features extracted, and the model characteristics may be analogous. However, at least one main difference between these steps may be that in the former, feature recognition, features are extracted from images and/or other visual content and model properties may be computed on images and associated features, but no classification is performed. On the other hand, the re-identification step is where the actual visual content classification step (i.e., the prediction of the identity of the subject and/or associated features or characteristics of the subject based on the visual content) using the tools described above by the feature recognition step, with the purpose of measuring if the altered visual content (e.g., anonymized visual content, anonymized images) may still be classified as the original input ones, which may enable the visual content module 150 and the practitioner to gain a perspective as to how much the visual content altering and/or anonymization steps have disturbed the input from a classification point of view. As will be explained in greater detail below, this perspective may be further utilized in adjusting the maximum number of iterations for the privacy-utility system particular visual content may require over time.

The results and/or output derived from the one or more feature recognition algorithms and/or the one or more feature re-identification algorithms utilized within the feature recognition component of the privacy-utility system are then passed to the evaluation component of the privacy-utility system. The results and/or output derived within the feature recognition component of the privacy-utility system may include, but are not limited to including, classification scores, feature importance, image segmentation, attention layers, and/or additional semantic features (e.g., inferred subject characteristics). These results and/or outputs may be derived from each of the one or more feature recognition algorithms and/or each of the one or more feature re-identification algorithms utilized within the feature recognition component, within the evaluation component of the privacy-utility system the visual content module may utilize calculations from the best performing, worst performing, and/or average of all the results and/or output derived from the feature recognition component algorithms to inform the practitioner of a current risk associated with the visual content associated with the subject and/or the altered visual content associated with the subject. The results and/or output derived in conjunction with the identified metadata, the selected downstream task, and/or prompt responses provided by the practitioner within the user interface may be utilized in determining the medical utility and/or optimal region for alterations and/or noise injections. The one or more feature recognition algorithms and/or the one or more feature re-identification algorithms utilized within the feature recognition component may be utilized to identify potential re-identification risks and/or whether the alterations and/or noise injections added to the visual content and/or altered visual content disrupted the potential re-identification risks in light of utility metrics. The utility metrics may be utilized to quantify a remaining risk and/or a trade-off between privacy and usefulness for the selected downstream task. The utility metrics may include, but are not limited to including, image similarity, distance metrics, downstream task region/features-of-interest similarity, subject characteristics, and/or Fitpatrick classifications, amongst other utility metrics. For example, in the case of medical utility, the visual content module 150 may extract the medical utility by applying a task-specific algorithm to the visual content, such as, a brain tumor classification, Lesion detection, pneumonia detection and/or if data may be embedded in the visual content that may references a particular task, such as, notes taken which indicate particular regions of interest) the visual content module 150 may additionally leverage the embedded data in the utility metric determination and/or of optimal locations for perturbations, adversarial patches, amongst other noise to be applied in altering the visual content associated with the subject.

Both visual attributes and/or recognition model features, such as model parameters and embeddings, may be utilized by the visual content module 150 in estimating the privacy and/or utility threshold. For example, the similarity score which may be estimated between embedding vectors derived from the feature recognition algorithms and machine learning models described above, changes in how the similarity score may be calculated for both perturbed images/altered visual content and the original images/original visual content which informs the visual content module 150 of lower utility and higher privacy. In another example, the visual content module 150 may keep track of inferred subject characteristics before and after perturbations and/or other alterations have been applied to the visual content associated with the subject. In this example, the important features that may not be altered in order to preserve the utility of the visual content are entered into the user interface by the practitioner and/or denoted within the visual content by the practitioner using the one or more image analysis tools described at step 202. The important features may which are to remain unaltered may also be derived by the visual content module 150 based on an identified downstream task. As will be explained in more detail below, the visual content module 150 may continuously learn over time which features are important based on a downstream task. In another example, the visual content module 150 may utilize an attention layer of the feature recognition models which may be represented as a two-dimensional depth map in which the most important image regions for the given task may be highlighted and the redundant ones may be suppressed (i.e., utilizing a heatmap displayed to a practitioner within the user interface). In this example, my comparing the attention map before and after the altering of the visual content and matching the perturbations and/or other altered regions with the Regions of Interest (ROI), which in this example may include relevant information for detecting a certain disease, both the visual content module 150 and the practitioner may estimate the significance of the alterations made to the visual content. The above examples are meant to be illustrative and not as a comprehensive list of the features and model properties which may be utilized by the visual content module 150.

The threshold component of the privacy-utility system evaluates whether the current risk associated with the calculations described above are greater than or equal to a privacy threshold. The privacy threshold may be a numerical value that may represent an unacceptable risk of re-identification. The privacy threshold may vary depending on the visual content associated with the subject. The privacy threshold may be set by a practitioner and/or an entity associated with the practitioner, such as, but not limited to, a hospital, doctor's office, amongst other entities which may desire setting their own privacy standards. The practitioner and/or entity may set the privacy threshold within the user interface. The visual content module 150 may also recommend different privacy thresholds to the practitioner and/or entity within the user interface based on, for example, industry standards, local and/or state laws, rules, regulations, and/or documents or other information provided by the practitioner and/or the entity. The threshold component may be utilized by the visual content module 150 in deciding whether the image meets a minimum level of privacy with respect to balancing utility for the downstream tasks identified by the practitioner within the user interface. The utility of the visual content associated with the subject may be a compound metric made up of multiple tasks, accordingly, the privacy threshold may be composed of conditions for individual tasks and/or for all tasks comprising the downstream tasks for which the visual content may be utilized by the practitioner. If the privacy threshold is not met, the visual content module 150 may pass the visual content to the visual content altering component of the privacy-utility system. The visual content module 150 may evaluate both the utility and the re-identification risk as compared to the privacy threshold. For example, the privacy threshold may require a subject recognition level less than 50 percent with a utility reduction no greater than 5 percent. In embodiments, where a practitioner may be interested in utilizing the visual content associated with the subject for two or more downstream tasks, the utility may be expressed as a compound metric summarizing (e.g., through weighted sum) the utility of each of the two or more downstream tasks. The privacy threshold in this embodiment may include unique rules targeting each of the particular tasks and/or may be guided by an overall utility across the two or more downstream tasks, such as, the utility of all tasks may not fluctuate by greater than 5 percent.

The visual content altering component of the privacy-utility system may receive the visual content associated with the subject and/or altered visual content associated with the subject below the privacy threshold. The visual content altering component may receive the feature recognizers and visual content which may be passed to a noise generator, which may be utilized by the visual content module 150 in at least adding and/or removing perturbations and/or patches to the visual content as directed by the evaluation component. In at least one embodiment, the perturbations, adversarial patches, and other noise may be added by modifying the RGB pixel values of the visual content using one or more open-source image manipulation libraries, such as, but not limited to, OpenCV™ (Open CV and all Open-CV-based trademarks or registered trademarks of Open Source Computer Vision Library in the United States and/or other countries), amongst others. The visual content module 150 may load the visual content as multidimensional arrays of floating point values which may represent at least red, green, and blue channels of the image and/or visual content. Ideal positions may be identified by iteratively applying a mask to the image during the visual content altering and/or anonymization process which may obscure different portions of the images and/or visual content, such that the original pixel values may not be modified, and computing which altered portion of the image and/or visual content provides the best performance and/or utility. Additionally, the visual content module 150 may further utilize attention maps and/or saliency maps which may be utilized to identify regions of influence of an image classification model, and such features (i.e., region of pixels) may be identified during the step described above which calculates the utility. In the example of a tumor classification model, the model may depend on pixels in the lower right region of a CT scan, in this example, a mask may be applied to this region which may preserve the integrity and utility of these pixels. Furthermore, the visual content module 150 may not necessarily remove ineffective patchers, perturbations, and/or other noise from the visual content, alternatively, the visual content module 150 may discard the visual content which may have been ineffectively altered and utilize new perturbations, patches, or noise on an original copy of the visual content associated with the subject received at step 202.

The altered visual content generated within the visual content altering component of the privacy-utility system may then be passed back through to the feature recognition component of the privacy-utility system by the visual content module 150. The noise enhanced and/or altered visual content may continuously pass through the components of the privacy-utility system until the visual content exceeds the privacy threshold which may balance the privacy and/or utility and/or after a maximum number of iterations has been reached. The maximum number of iterations may be set by the practitioner and/or the entity associated with the practitioner within the user interface. As will be explained in more detail below, the practitioner may also alter the visual content in response to the altered visual content failing to meet the privacy threshold after the maximum number of iterations for the privacy-utility system has been reached.

In an embodiment, the practitioner may also alter the visual content using the one or more image analysis d described at step 202. In this embodiment, the practitioner may utilize the one or more image analysis tools described at step 202 throughout the process. The practitioner may alter the visual content associated with the subject prior to the altering by the visual content module 150 at step 204 and/or in response to the analytics provided at step 206. For example, prior to the alterations made by the visual content module 150 at step 204 the practitioner may utilize the one or more image analysis tools to crop the visual content to limit the amount of visual content to just the areas for which the practitioner desires an external consultation and/or third party opinion.

The visual content module 150 may utilize at least, one or more of, the downstream tasks identified by the practitioner, alterations made by the practitioner for specific downstream tasks, perturbations and/or adversarial patches amongst other noise present within the altered visual content exceeding the privacy threshold, and/or comparisons of the original visual content and altered visual content in training the one or more adversarial machine learning algorithms utilized in privatizing the visual content associated with the subject. The evaluation component of the privacy-utility system may be continuously trained and/or retrained over time to optimize a choice of privacy thresholds specific to different downstream tasks and/or specific practitioners. Threshold and importance of particular features corresponding to specific downstream tasks may be iteratively fine-tuned by the practitioner, who may update scores related to a specific condition based on the practitioners practice and/or local changes in privacy regulation. Furthermore, the visual content module 150 may utilize a web-crawler and/or other search mechanism, leveraging IBM Watson® Speech Recognition (IBM Watson® and all Watson-based trademarks are trademarks or registered trademarks of International Business Machines Corporation in the United States, and/or other countries), IBM Watson® Speech to Text, IBM Watson® Text to Speech, amongst other content identification mechanisms in notifying the practitioner directly within the user interface as to local, state, and/or federal changes in privacy regulations such that the described invention may not violate or encourage the violation of any local, state, federal, or international law with respect to privacy protection. Additionally, ancillary information and/or metadata can be used to assist in the classification steps, but may be considered option for the purpose of this invention. Examples may include, but are not limited to including, textual reports associated with the visual content and regions of interest specified within the visual content and/or associated downstream task.

At 206, the visual content module 150 presents the altered visual content associated with the subject to the practitioner within the user interface. The visual content module 150 may present the analytics associated with the analysis of the altered visual content and the altered visual content to the practitioner. The altered visual content may be presented to the practitioner after the altered visual content exceeds the threshold and/or the maximum number of iterations for the privacy-utility system cycle are met.

The visual content module 150 may present the analytics to the practitioner within the user interface. The analytics may include, but are not limited to including, the determined re-identification risk associated with the altered visual content, the re-identification risk in comparison to the privacy threshold, the utility reduction of the altered visual content in comparison to the original visual content for each of the downstream tasks identified by the practitioner, metadata extracted from the visual content, classification scores, feature scores, image segmentation, attention layers, and/or other metrics derived within the feature recognition component of the privacy-utility system.

In response to the analytics, the practitioner may adjust the levels of acceptable utility reduction and/or the privacy threshold within the user interface. The practitioner may also have the ability to store each version of the altered visual content within database 130 such that the practitioner may evaluate multiple versions of the altered visual content prior to the visual content being shared and/or transmitted to external consultants and/or other institutions. Additionally, as described in detail above with respect to at least step 204, the practitioner may further alter the altered visual content within the user interface using the one or more image analysis tools described at step 202 and/or by manually adding perturbations, adversarial patches, and/or other noise to the altered visual content. As will be explained in more detail below, the version of the altered visual content which is transmitted to the external consultants and/or other institutions may be utilized in retraining the one or more machine learning models utilized by the privacy-utility system and described at step 204, such that, for example, the adversarial machine learning algorithms may learn and improve the manner by which perturbations, adversarial patches, and/or other noise are added to the visual content for specific downstream tasks and/or specific practitioners.

Additionally, while the one or more machine learning models utilized by the privacy utility system are being trained the visual content module 150 may present the altered visual content as well as one or more additional recommendations with may be implemented by the practitioner within the user interface using the one or more image analysis tools. For example, the visual content module 150 may present the analytics associated with the altered visual content as well as additional edits that may be made to the altered visual content. The visual content module 150 may include projected analytics for each of the additional edits such that the practitioner may evaluate the privatization benefits versus the utility drawbacks of each of the additional edits. The implementation and/or rejections of the additional edits and/or other recommendations presented by the visual content module 150 to the user may also be utilized in further training the one or more machine learning models associated with the privacy utility system.

In an embodiment, the user interface may be presented to the practitioner by the visual content module 150 utilizing Virtual Reality (VR) and/or Augmented Reality (AR) on one or more EUDs 103, the one or more EUDs 103 may be a VR and/or AR compatible device, including, but not limited to including, smart glasses, smart headsets, smart phones, and/or other VR and/or AR compatible devices, as well as Extended Reality (XR) and mixed reality (MR). Accessing the user interface through the one or more EUDs 103 described above may require a username and password specific to the practitioner such that the privacy of the visual content may be preserved. An additional password or security clearance may be required to retrieve visual content and/or other data from the database 130 and/or transmit the visual content to the third party. The visual content module 150 may retrieve the original visual content, altered visual content, and/or the corresponding analytics from the database 130. The practitioner may evaluate the altered visual content, original visual content, multiple versions of the visual content, additional edits, recommendations, and the analytics associated with each version of the original visual content and/or altered visual content within the user interface. The EUDs 103 described above may enable the practitioner to interactively evaluate the altered visual content such that the practitioner may evaluate the altered visual content, additional edits, recommendations, the analytics associated with each version of the altered visual content, and/or leverage the one or more image analysis tools described at step 202 within an interactive environment. The visual content module 150 may leverage these interactive capabilities in allowing the practitioner to efficiently swipe through different versions of the altered visual content, evaluate recommendations, and/or select the altered visual content to be transmitted to the third party. In this embodiment, the practitioner may be able to select and directly transmit the altered visual content to the third party using the EUD 103.

The interactions and/or actions during the evaluation process by the practitioner within the user interface as well as the selected altered visual content to be transmitted to the third party may be utilized in additional training and/or retraining of the one or more adversarial machine learning algorithms and/or the one or more other machine learning models utilized by the privacy-utility system described above, specifically with respect to step 204. The interactions by the practitioner and the selected altered visual content may be saved to the database 130. The visual content module 150 may utilize this data in further building the database 130 for the specific practitioner, specific downstream tasks, amongst other categories such that the one or more adversarial machine learning algorithms and/or the one or more other machine learning models utilized by the privacy-utility system may be specifically trained according to at least, practitioners, tasks, institutions, amongst other fields. For example, the practitioner may swipe between altered visual content, zoom in on particular regions of the altered visual content, accept noise recommendations, amongst other interactions within the user interface. The visual content module 150 may store this information and not only utilize the data in retraining the one or more adversarial machine learning algorithms and/or the one or more other machine learning models utilized by the privacy-utility system for the practitioner specifically but also for similar visual content to be transmitted to a third party in the future such that the image anonymization process may become more automated with each iteration. For example, based on the actions associated with the evaluation by the practitioner within the user interface, such as additional edits or accepting recommendations, the visual content module 150 may additionally train and/or retrain the one or more machine learning models utilized by the privacy-utility system such that the one or more machine learning models may improve future alterations to new visual content in a manner specific to a downstream task or the practitioner. In this example, the future alterations to the new visual content received may improve the utility, privacy, and save the practitioner time. These improvements may continue for the specific practitioner as the practitioner's style and preferences are learned by the machine learning models, as well as for other practitioners which may benefit from the improved machine learning models by maximizing utility, minimizing reidentification risk, and reduced evaluation times. In the case of new practitioners this may be particularly useful in avoiding privacy violations.

At 208, the visual content module 150 transmits the altered visual content to a third party. The altered visual content transmitted to the third party may be based on the selection and/or approval of the practitioner at step 206. The third party may be an external consultant, external institution, and/or any third-party in which the practitioner and/or the entity associated with the practitioner desires to receive the altered visual content while maintaining the anonymity of the subject associated with the altered visual content.

The visual content module 150 may utilize the existing infrastructure utilized by the practitioner and/or entity associated with the practitioner, a hybrid cloud based service such as, but not limited to, IBM Cloud® (IBM Cloud® and all IBM-based trademarks are trademarks or registered trademarks of International Business Machines Corporation in the United States, and/or other countries), the infrastructure of an existing application in which the visual content module 150 may be an add-on solution, amongst other methods in transmitting the altered visual content to a third party.

The visual content module 150 may monitor feedback received from the third party with respect to the altered visual content. The practitioner may enable the visual content module 150 to monitor discussions between the practitioner and the third party. For audio and/or visual content the visual content module 150 may utilize tools such as, but not limited to, IBM Watson® Speech Recognition (IBM Watson® and all Watson-based trademarks are trademarks or registered trademarks of International Business Machines Corporation in the United States, and/or other countries), IBM Watson® Speech to Text, IBM Watson® Text to Speech, IBM Watson® Tone Analyzer, IBM Watson® Natural Language Understanding, IBM Watson® Natural Language Processing, amongst other mechanisms in understanding the discussions between the practitioner and the third party. The visual content module 150 may utilize other Natural Language Processing (NLP) techniques, such as those implemented in IBM Watson® (IBM Watson® and all Watson-based trademarks are trademarks or registered trademarks of International Business Machines Corporation in the United States, and/or other countries) in understanding textual and/or additional feedback received from the third party in monitoring the feedback with respect to the altered visual content. The visual content module 150 may utilize at least the techniques described above as well as other information in performing a sentiment analysis with respect to the altered visual content. The visual content module 150 may utilize the determined sentiment (i.e., negative, neutral, positive) in further retraining the one or more adversarial machine learning algorithms and/or the one or more other machine learning models utilized by the privacy-utility system. The feedback also may be stored in the database 130 and utilized in flagging similar altered visual content in the future.

For example, Practitioner 1 may have sent Altered Visual Content 1 to Third-Party Evaluator 1 in order receive another opinion. Based on the feedback received from the Third Party Evaluator 1 to Practitioner 1 the visual content module 150 may have assigned a negative sentiment. Additionally, in response to the negative sentiment, Practitioner 1 sent Altered Visual Content 2 to Third-Party Evaluator 1. Altered Visual Content 2 may have been assigned a positive sentiment by the visual content module 150 and allowed Practitioner 1 to provide recommendations and/or a treatment plan to the subject associated with Altered Visual Content 1 and 2. In this example, the visual content module 150 may utilize both Altered Visual Content 1 and Altered Visual Content 2 as well as their corresponding sentiments in retraining the one or more adversarial machine learning algorithms and/or the one or more other machine learning models utilized by the privacy-utility system. In the future, for either similar tasks, Practitioner 1, or altered visual content being sent to Third-Party Evaluator 1 the one or more adversarial machine learning algorithms and/or the one or more other machine learning models utilized by the privacy-utility system may apply perturbations, adversarial patches, and/or other noise similar to those applied in Altered Visual Content 2 as opposed to Altered Visual Content 1.

As the visual content module 150 receives feedback from the practitioner and/or third-party evaluators the visual content module 150 may automatically adjust the levels of acceptable utility reduction and/or the privacy threshold such that future altered visual content has higher utility and lower risk of re-identification. Additionally, the visual content module 150 may improve recommended edits displayed to a practitioner within the user interface and learn edits likely to be accepted by particular practitioners and/or for particular tasks such that the visual content module 150 may reduce the number of versions of the altered visual content presented to the user within the user interface and reduce the number of iterations visual content requires within the privacy-utility system.

Figure 3:
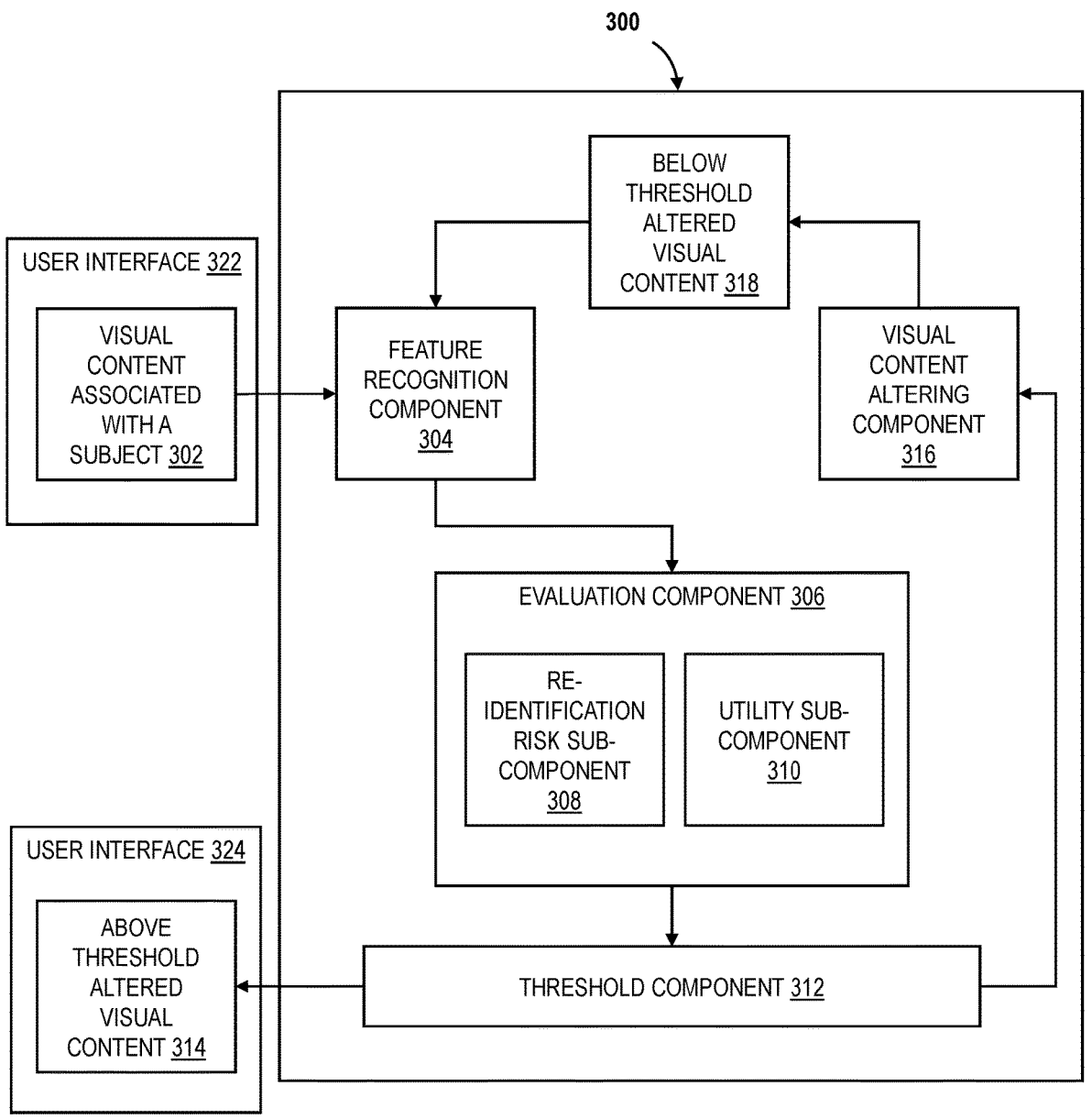
FIG. 3 is an operational flowchart illustrating a process for altering visual content within a privacy-utility system according to at least one embodiment.

Referring now to FIG. 3, an operational flowchart illustrating the process for altering the visual content within the privacy-utility system 300 utilized by the visual content module 150 according to at least one embodiment is depicted.

The privacy-utility system 300 utilized by the visual content module 150 in altering the visual content associated with the subject 302 may be described in more detail above with respect to at least step 204 of the visual content privatization process 200. The privacy-utility system 300 may be comprised of several components, including, but not limited to, a feature recognition component 304, an evaluation component 306, a threshold component 312, and/or a visual content altering component 316. The evaluation component 306 may be further comprised of at least two sub-components, the re-identification risk sub-component 308 and the utility sub-component 310.

The visual content associated with a subject 302 may be retrieved from the database 130 using one or more click actions and/or other commands performed by the practitioner within the user interface 322 which may be accessed using one or more EUDs 103, described in greater detail above with respect to at least steps 202 and 204.

The feature recognition component 304 may receive as input the visual content associated with the subject 302 selected by the practitioner within the user interface 322. The feature recognition component 304 may utilize one or more feature recognition algorithms and/or one or more feature re-identification algorithms in accessing an initial privacy risk associated with the visual content associated with the subject. The one or more feature recognition algorithms which may be utilized by the visual content module within the feature recognition component 322 are described in greater detail above with respect to at least step 204.

The results and/or output derived from the one or more feature recognition algorithms and/or the one or more feature re-identification algorithms utilized within the feature recognition component 304 of the privacy-utility system 300 are then passed to the evaluation component 306 of the privacy-utility system 300. In this embodiment, the evaluation component 306 may be comprised of at least two sub-components, the re-identification risk sub-component

308 and the utility sub-component 310. The evaluation component 306 and the sub-components comprising it are utilized in at least quantifying a risk and/or trade-off between the privacy and usefulness of the visual content for a downstream task previously identified by the practitioner within the user interface 322. The evaluation component 306 may be responsible for evaluating an original version of the visual content associated with the subject and/or visual content associated with the subject previously determined to be below the privacy threshold in a previous iteration of the cycle illustrated by the privacy-utility system 300.

The threshold component 312 of the privacy-utility system 300 evaluates whether the current risk associated with the calculations described above at step 204 are greater than or equal to a privacy threshold. The privacy threshold may be a numerical value that may represent an unacceptable risk of re-identification. The privacy threshold may vary depending on the visual content associated with the subject. The privacy threshold may be set by a practitioner and/or an entity associated with the practitioner, such as, but not limited to, a hospital, doctor's office, amongst other entities which may desire setting their own privacy standards. The practitioner and/or entity may set the privacy threshold within the user interface 322.

If the privacy threshold is met, the visual content module 150 may present the above threshold altered visual content 314 to the practitioner within the user interface 324. Although, the user interface 324 is depicted separately from user interface 322 they may refer to the same user interface. Although user interface 322 may be accessed on a different EUD 103 than user interface 324. As described in greater detail at step 206, the practitioner may utilize an EUD 103 with VR and/or AR capabilities, such as, but not limited to including, smart glasses, smart headsets, smart phones, and/or other VR and/or AR compatible devices, as well as Extended Reality (XR) and mixed reality (MR), such that the practitioner may interact with the above threshold altered visual content 314 before it is transmitted to a third-party.

Alternatively, if the privacy threshold is not met, the visual content module 150 may pass the visual content to the visual content altering component 316 of the privacy-utility system 300. The visual content altering component 316 of the privacy-utility system 300 may receive the visual content associated with the subject 302 and/or altered visual content associated with the subject below the privacy threshold 318. The visual content altering component 316 may receive the feature recognizers and visual content which may be passed to a noise generator, which may be utilized by the visual content module 150 in adding perturbations, adversarial patches, and/or other noise to the visual content associated with the subject 302 and/or altered visual content associated with the subject below the privacy threshold 318.

The visual content associated with the subject 302 and/or altered visual content associated with the subject below the privacy threshold 318 may then be passed back through to the feature recognition component 304 of the privacy-utility system 300 by the visual content module 150. The noise enhanced and/or altered visual content may continuously pass through the components of the privacy-utility system 300 until the visual content meets the threshold component 312 which may balance the privacy and/or utility and/or after a maximum number of iterations has been reached described in greater detail above with respect to the evaluation component 306 and step 204 of the image anonymization process 200. The maximum number of iterations may be set by the practitioner and/or the entity associated with the practitioner within the user interface 322 and/or 324. As will be explained in more detail below, the practitioner may also alter the visual content in response to the altered visual content failing to meet the privacy threshold after the maximum number of iterations for the privacy-utility system has been reached within the user interface 322 and/or 324.

It may be appreciated that FIGS. 2 and 3 provide only an illustration of one embodiment and do not imply any limitations with regard to how different embodiments may be implemented. Many modifications to the depicted embodiment(s) may be made based on design and implementation requirements.

Various aspects of the present disclosure are described by narrative text, flowcharts, block diagrams of computer systems and/or block diagrams of the machine logic included in computer program product (CPP) embodiments. With respect to any flowcharts, depending upon the technology involved, the operations can be performed in a different order than what is shown in a given flowchart. For example, again depending upon the technology involved, two operations shown in successive flowchart blocks may be performed in reverse order, as a single integrated step, concurrently, or in a manner at least partially overlapping in time.

A computer program product embodiment ("CPP embodiment" or "CPP") is a term used in the present disclosure to describe any set of one, or more, storage media (also called "mediums") collectively included in a set of one, or more, storage devices that collectively include machine readable code corresponding to instructions and/or data for performing computer operations specified in a given CPP claim. A "storage device" is any tangible device that can retain and store instructions for use by a computer processor. Without limitation, the computer readable storage medium may be an electronic storage medium, a magnetic storage medium, an optical storage medium, an electromagnetic storage medium, a semiconductor storage medium, a mechanical storage medium, or any suitable combination of the foregoing. Some known types of storage devices that include these mediums include: diskette, hard disk, random access memory (RAM), read-only memory (ROM), erasable programmable read-only memory (EPROM or Flash memory), static random access memory (SRAM), compact disc read-only memory (CD-ROM), digital versatile disk (DVD), memory stick, floppy disk, mechanically encoded device (such as punch cards or pits/lands formed in a major surface of a disc) or any suitable combination of the foregoing. A computer readable storage medium, as that term is used in the present disclosure, is not to be construed as storage in the form of one or more transitory signals per se, such as radio waves or other freely propagating electromagnetic waves, electromagnetic waves propagating through a waveguide, light pulses passing through a fiber optic cable, electrical signals communicated through a wire, and/or other transmission media. As will be understood by those of skill in the art, data is typically moved at some occasional points in time during normal operations of a storage device, such as during access, de-fragmentation or garbage collection, but this does not render the storage device as transitory because the data is not transitory while it is stored.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope of the described embodiments. The terminology used herein was chosen to best explain the principles of the embodiments, the practical application or technical improvement over technologies found in the marketplace, or to enable others of ordinary skill in the art to understand the embodiments disclosed herein.

The present disclosure shall not be construed as to violate or encourage the violation of any local, state, federal, or international law with respect to privacy protection.

What is claimed is:

1. A method for visual content privatization, the method comprising:

receiving visual content associated with a subject;

altering the visual content using at least one or more image perturbations or one or more adversarial patches in response to a practitioner requesting an external consultation from a third party, wherein the visual content is altered within a privacy-utility system comprised of a feature recognition component and a visual content altering component, wherein the visual content altering component implements a level of noise within the visual content such that the altered visual content is misclassified by a trained classification model, and wherein the feature recognition component utilizes one or more feature recognition algorithms and one or more feature re-identification algorithms;

presenting an altered visual content to the practitioner within a user interface including analytics associated with the altered visual content and one or more additional recommendations, wherein the analytics and one or more recommendations are generated using one or more machine learning models;

transmitting the altered visual content to the third party following an approval by the practitioner; and retraining the one or more machine learning models based on the one or more additional recommendations implemented and not implemented by the practitioner.

2. The method of claim 1, wherein altering the visual content in response to the practitioner requesting the external consultation further comprises:

displaying one or more prompts to the practitioner in the user interface, wherein the one or more prompts are designed to gather information about a downstream task, wherein adversarial algorithms, including a Fast Gradient Sign Method (FGSM), and utility metrics are leveraged in altering the visual content based on the downstream task.

3. The method of claim 2, wherein the altered visual content presented to the practitioner maximizes a utility of the visual content for the downstream task and minimizes a reidentification risk of the subject associated with the visual content, wherein a degree of the image perturbations, locations, and pervasiveness are throttled depending on the downstream task.

4. The method of claim 2, wherein the retraining of the one or more machine learning models further utilizes interactions and actions of the practitioner within the user interface during an evaluation process to fine tune the one or more machine learning models specifically to the practitioner or the downstream task.

5. The method of claim 1, wherein the privacy-utility system is further comprised of an evaluation component and a threshold component.

6. The method of claim 1, wherein the approval by the practitioner is received in the user interface following an evaluation by the practitioner of the altered visual content in an interactive environment within the user interface.

7. The method of claim 6, wherein actions associated with the evaluation by the practitioner are utilized for additional training of the one or more machine learning models, such that the one or more machine learning models improve future alterations to new visual content in a manner specific to a downstream task or the practitioner.

8. The method of claim 1, wherein the practitioner may adjust levels of acceptable utility reduction and a privacy threshold within the user interface based on the analytics associated with the altered visual content.

9. A computer system for visual content privatization, comprising:

one or more processors, one or more computer-readable memories, one or more computer-readable tangible storage medium, and program instructions stored on at least one of the one or more tangible storage medium for execution by at least one of the one or more processors via at least one of the one or more memories, wherein the computer system is capable of performing a method comprising:

program instructions, stored on at least one of the one or more computer-readable storage media for execution by at least one of the one or more processors via at least one of the one or more memories, to receive visual content associated with a subject;

program instructions, stored on at least one of the one or more computer-readable storage media for execution by at least one of the one or more processors via at least one of the one or more memories, to alter the visual content using at least one or more image perturbations or one or more adversarial patches in response to a practitioner requesting an external consultation from a third party, wherein the visual content is altered within a privacy-utility system comprised of a feature recognition component and a visual content altering component, wherein the visual content altering component implements a level of noise within the visual content such that the altered visual content is misclassified by a trained classification model, and wherein the feature recognition component utilizes one or more feature recognition algorithms and one or more feature re-identification algorithms;

program instructions, stored on at least one of the one or more computer-readable storage media for execution by at least one of the one or more processors via at least one of the one or more memories, to present an altered visual content to the practitioner within a user interface including analytics associated with the altered visual content and one or more additional recommendations, wherein the analytics and one or more recommendations are generated using one or more machine learning models;

program instructions, stored on at least one of the one or more computer-readable storage media for execution by at least one of the one or more processors via at least one of the one or more memories, to transmit the altered visual content to the third party following an approval by the practitioner; and program instructions, stored on at least one of the one or more computer-readable storage media for execution by at least one of the one or more processors via at least one of the one or more memories, to retrain the one or more machine learning models based on the one or more additional recommendations implemented and not implemented by the practitioner.

10. The computer system of claim 9, wherein the program instructions to alter the visual content in response to the practitioner requesting the external consultation further comprises:

program instructions, stored on at least one of the one or more computer-readable storage media for execution by at least one of the one or more processors via at least one of the one or more memories, to display one or more prompts to the practitioner in the user interface, wherein the one or more prompts are designed to gather information about a downstream task, wherein adversarial algorithms, including a Fast Gradient Sign Method (FGSM), and utility metrics are leveraged in altering the visual content based on the downstream task.

11. The computer system of claim 10, wherein the altered visual content presented to the practitioner maximizes a utility of the visual content for the downstream task and minimizes a reidentification risk of the subject associated with the visual content, wherein a degree of the image perturbations, locations, and pervasiveness are throttled depending on the downstream task.

12. The computer system of claim 9, wherein the privacy-utility system is further comprised of an evaluation component and a threshold component.

13. The computer system of claim 9, wherein the approval by the practitioner is received in the user interface following an evaluation by the practitioner of the altered visual content in an interactive environment within the user interface.

14. The computer system of claim 13, wherein actions associated with the evaluation by the practitioner are utilized for additional training of the one or more machine learning models, such that the one or more machine learning models improve future alterations to new visual content in a manner specific to a downstream task or the practitioner.

15. A computer program product for visual content privatization, comprising:

one or more computer readable storage media, and program instructions collectively stored on the one or more computer readable storage media, the program instructions comprising:

program instructions, stored on at least one of the one or more computer-readable storage media, to receive visual content associated with a subject;

program instructions, stored on at least one of the one or more computer-readable storage media, to alter the visual content using at least one or more image perturbations or one or more adversarial patches in response to a practitioner requesting an external consultation from a third party, wherein the visual content is altered within a privacy-utility system comprised of a feature recognition component and a visual content altering component, wherein the visual content altering component implements a level of noise within the visual content such that the altered visual content is misclassified by a trained classification model, and wherein the feature recognition component utilizes one or more feature recognition algorithms and one or more feature re-identification algorithms;

program instructions, stored on at least one of the one or more computer-readable storage media, to present an altered visual content to the practitioner within a user interface including analytics associated with the altered visual content and one or more additional recommendations, wherein the analytics and one or more recommendations are generated using one or more machine learning models;

program instructions, stored on at least one of the one or more computer-readable storage media, to transmit the altered visual content to the third party following an approval by the practitioner; and program instructions, stored on at least one of the one or more computer-readable storage media, to retrain the one or more machine learning models based on the one or more additional recommendations implemented and not implemented by the practitioner.

16. The computer program product of claim 15, wherein the program instructions to alter the visual content in response to the practitioner requesting the external consultation further comprises:

program instructions, stored on at least one of the one or more computer-readable storage media, to display one or more prompts to the practitioner in the user interface, wherein the one or more prompts are designed to gather information about a downstream task, wherein adversarial algorithms, including a Fast Gradient Sign Method (FGSM), and utility metrics are leveraged in altering the visual content based on the downstream task.

17. The computer program product of claim 16, wherein the altered visual content presented to the practitioner maximizes a utility of the visual content for the downstream task and minimizes a reidentification risk of the subject associated with the visual content, wherein a degree of the image perturbations, locations, and pervasiveness are throttled depending on the downstream task.

18. The computer program product of claim 15, wherein the privacy-utility system is further comprised of an evaluation component and a threshold component.

19. The computer program product of claim 15, wherein the approval by the practitioner is received in the user interface following an evaluation by the practitioner of the altered visual content in an interactive environment within the user interface.

* * * * *